(12) United States Patent
Dees

(10) Patent No.: US 9,119,734 B2
(45) Date of Patent: Sep. 1, 2015

(54) TRIAL FEMORAL PROSTHESIS AND ITS USE

(75) Inventor: Roger Ryan Dees, Senatobia, MS (US)

(73) Assignee: Smith & Nephew, Inc., Memphis, TN (US)

( * ) Notice: Subject to any disclaimer, the term of this patent is extended or adjusted under 35 U.S.C. 154(b) by 960 days.

(21) Appl. No.: 12/160,319

(22) PCT Filed: Oct. 31, 2006

(86) PCT No.: PCT/US2006/042705
§ 371 (c)(1),
(2), (4) Date: Aug. 22, 2008

(87) PCT Pub. No.: WO2008/054389
PCT Pub. Date: May 8, 2008

(65) Prior Publication Data
US 2011/0307067 A1   Dec. 15, 2011

(51) Int. Cl.
*A61B 17/58* (2006.01)
*A61B 17/60* (2006.01)
*A61F 2/00* (2006.01)
*A61F 2/38* (2006.01)
*A61F 2/46* (2006.01)
*A61B 17/15* (2006.01)
(Continued)

(52) U.S. Cl.
CPC ............. *A61F 2/4684* (2013.01); *A61B 17/155* (2013.01); *A61B 17/1764* (2013.01); *A61F 2/3859* (2013.01); *A61F 2002/30616* (2013.01); *A61F 2310/00023* (2013.01); *A61F 2310/00029* (2013.01); *A61F 2310/00089* (2013.01); *A61F 2310/00161* (2013.01)

(58) Field of Classification Search
USPC ......... 606/86 R, 88, 89, 87; 623/20.24–20.31
See application file for complete search history.

(56) References Cited

U.S. PATENT DOCUMENTS

| D273,894 S | 5/1984 | Kenna |
| D273,895 S | 5/1984 | Kenna |
| D274,090 S | 5/1984 | Kenna |

(Continued)

FOREIGN PATENT DOCUMENTS

| FR | 2 742 037 | 6/1997 |
| WO | WO 95/33414 | 12/1995 |

(Continued)

OTHER PUBLICATIONS

Brochure entitled Aesculap EnduRo Gekoppelte Knieendoprothese Aesculap Orthopaedics B/Braun Sharing Expertise, 8 pages. (known prior to Jul. 16, 2010).

(Continued)

*Primary Examiner* — Andrew Yang
*Assistant Examiner* — Diana S Jones
(74) *Attorney, Agent, or Firm* — Krieg DeVault LLP

(57) ABSTRACT

Embodiments of the present application relate generally to provisional orthopedic components, and specifically, to a trial system including a cam module (10) and a trial femoral component (100) that can be used during joint replacement surgery. The systems and methods described help a surgeon prepare a patient's bone to receive a permanent implant by providing a system that can be used to guide preparatory box cuts, and that can then be completed with a cam module (10)—without removal from the patient's bone—so that the same component can be used for the trialing process.

18 Claims, 11 Drawing Sheets

(51) Int. Cl.
*A61B 17/17* (2006.01)
*A61F 2/30* (2006.01)

(56) References Cited

U.S. PATENT DOCUMENTS

| | | |
|---|---|---|
| D274,091 S | 5/1984 | Kenna |
| D274,092 S | 5/1984 | Kenna |
| D274,093 S | 5/1984 | Kenna |
| D274,094 S | 5/1984 | Kenna |
| D274,095 S | 5/1984 | Kenna |
| D274,161 S | 6/1984 | Kenna |
| D274,162 S | 6/1984 | Kenna |
| 4,550,448 A | 11/1985 | Kenna |
| 4,646,729 A | 3/1987 | Kenna et al. |
| 4,653,488 A | 3/1987 | Kenna |
| 4,668,290 A | 5/1987 | Wang et al. |
| 4,714,468 A | 12/1987 | Wang et al. |
| 4,721,104 A | 1/1988 | Kaufman et al. |
| 4,722,330 A | 2/1988 | Russell et al. |
| 4,787,383 A | 11/1988 | Kenna |
| 4,825,857 A | 5/1989 | Kenna |
| 4,834,756 A | 5/1989 | Kenna |
| 4,926,847 A | 5/1990 | Luckman |
| 4,944,756 A | 7/1990 | Kenna |
| 5,035,700 A | 7/1991 | Kenna |
| 5,100,409 A | 3/1992 | Coates et al. |
| 5,176,684 A | 1/1993 | Ferrante |
| 5,192,324 A | 3/1993 | Kenna |
| 5,344,461 A | 9/1994 | Philipot |
| 5,441,537 A | 8/1995 | Kenna |
| 5,458,637 A | 10/1995 | Hayes |
| 5,458,645 A | 10/1995 | Bertin |
| 5,542,947 A | 8/1996 | Treacy |
| 5,569,259 A | 10/1996 | Ferrante |
| 5,624,444 A | 4/1997 | Wixon et al. |
| 5,662,656 A | 9/1997 | White |
| 5,683,397 A | 11/1997 | Vendrely et al. |
| 5,709,689 A | 1/1998 | Ferrante et al. |
| 5,716,361 A | 2/1998 | Masini |
| 5,720,752 A | 2/1998 | Elliott et al. |
| 5,743,915 A | 4/1998 | Bertin et al. |
| 5,769,854 A | 6/1998 | Bastian et al. |
| 5,769,855 A | 6/1998 | Bertin et al. |
| 5,776,201 A * | 7/1998 | Colleran et al. ............ 623/20.15 |
| 5,810,829 A | 9/1998 | Elliott et al. |
| 5,810,831 A | 9/1998 | D'Antonio |
| 5,860,980 A | 1/1999 | Axelson, Jr. et al. |
| 5,935,132 A | 8/1999 | Bettuchi et al. |
| 5,944,722 A | 8/1999 | Masini |
| 5,957,926 A | 9/1999 | Masini |
| 6,013,081 A | 1/2000 | Burkinshaw et al. |
| 6,077,270 A | 6/2000 | Katz |
| 6,102,916 A | 8/2000 | Masini |
| 6,187,010 B1 | 2/2001 | Masinie |
| 6,217,618 B1 | 4/2001 | Hileman |
| 6,290,704 B1 | 9/2001 | Burkinshaw et al. |
| 6,458,135 B1 | 10/2002 | Harwin et al. |
| 6,488,687 B1 | 12/2002 | Masini |
| 6,503,254 B2 | 1/2003 | Masini |
| 6,558,391 B2 | 5/2003 | Axelson, Jr. et al. |
| 6,575,980 B1 | 6/2003 | Robie et al. |
| 6,629,999 B1 | 10/2003 | Scrafin, Jr. |
| 6,740,092 B2 | 5/2004 | Lombardo et al. |
| 6,783,551 B1 | 8/2004 | Metzger et al. |
| 6,827,739 B2 * | 12/2004 | Griner et al. ............... 623/16.11 |
| 2004/0039450 A1 | 2/2004 | Griner et al. |
| 2004/0153087 A1 | 8/2004 | Sanford et al. |
| 2004/0260301 A1 | 12/2004 | Lionberger et al. |
| 2005/0075736 A1 * | 4/2005 | Collazo ..................... 623/20.16 |
| 2006/0173463 A1 | 8/2006 | Dees |
| 2006/0265078 A1 * | 11/2006 | McMinn ..................... 623/20.14 |
| 2008/0167722 A1 | 7/2008 | Metzger et al. |
| 2009/0088860 A1 | 4/2009 | Romeis et al. |
| 2009/0125114 A1 | 5/2009 | May et al. |
| 2009/0143866 A1 | 6/2009 | Servidio |

FOREIGN PATENT DOCUMENTS

| | | |
|---|---|---|
| WO | WO 97/30640 A1 | 8/1997 |
| WO | WO 97/30648 A1 | 8/1997 |
| WO | WO 98/32384 A1 | 7/1998 |
| WO | WO 99/20192 A1 | 4/1999 |
| WO | WO 00/13594 A1 | 3/2000 |
| WO | WO 2008/54389 | 5/2008 |

OTHER PUBLICATIONS

Brochure entitled Aesculap EnduRo Gekoppelte Knieendoprothese Operationstechnik Aesculap Orthopaedics B/Braun Sharing Expertise, 56 pages. (known prior to Jul. 16, 2010).
Brochure entitled Aesculap EnduRo Rotating Hinge Knee Endoprothesis Manual surgical procedure, 01 page B/Braun Sharing Expertise (known prior to Jul. 16, 2010).
Photograph of Aesculap-B Braun EnduRo Knee—rotating hinge (known prior to Jul. 16, 2010).
Chinese Patent Application No. 200680056847.5, Office Action dated Nov. 9, 2010.
International Search Report in related International Application No. PCT/US2006/042705.
T-1™ Instrumentation, 01 page (undated).
Brochure entitled 'Ascent™ Total Knee System Anterior Referencing Surgical Technique,' Surgical Technique by Rick Basset, M.D. and Michael Jacobs, M.D., Taking total knee replacement to new heights, Biomet Orthopedics, Inc., 28 pages. (2000).
Brochure entitled 'Monogram® Knee Instruments,' Stryker Howmedica Osteonics, Monogram® IM Revision Instrument Surgical Technique with Offsetting Instruments Total Stabilizer, 32 pages (1999).
Brochure entitled 'NexGen® System Complete Knee Solution,' LCCK NexGen® Complete Knee Solution Revision Instrumentation Surgical Technique for Legacy® Knee Constrained Condylar Knee, Zimmer, 60 pages. (2001).
Examination Report, Australian Patent Application No. 2006350235, 2 pages.
International Preliminary Report on Patentability; PCT/US2006/042705; May 5, 2009; 7 pages.
First Examination Report; European Patent Office; European Patent Application No. 06836779.6; Feb. 25, 2013; 6 pages.

* cited by examiner

TRIAL FEMORAL PROSTHESIS AND ITS USE

CROSS REFERENCE TO RELATED APPLICATION

This application is the United States national phase of International Application No. PCT/US2006/042705 filed on Oct. 31, 2006 and published in English on May 8, 2008 as International Publication No. WO 2008/054389 A1, the contents of which are hereby incorporated by reference.

BACKGROUND OF THE INVENTION

Embodiments of the present invention relate generally to provisional orthopedic components, and specifically, to a trial system that can be used during joint replacement surgery. The systems and methods described help a surgeon prepare a patient's bone to receive a permanent implant by providing a system that can be used to guide preparatory cuts, as well as to correctly determine the fit of the implant to be used.

The use of implant provisional components (also referred to as "trial components") is common during joint replacement surgery. They are used to test the fit and alignment of an implant with a bone that has been reshaped by a surgeon. Although the actual implant to be used could serve these purposes, the use of trial or provisional components eliminates the risk that the actual implants will be damaged. Trial components also prevent the surgeon from having to introduce the actual components into the surgical field until the precise size of the component that will be needed is determined, saving sterilization costs and protecting the implants.

One common type of joint replacement surgery is knee surgery. In total knee joint replacement surgery, a surgeon typically affixes two prosthetic components to the patient's bone structure: a first to the patient's femur (the femoral component) and a second to the patient's tibia (the tibial component). The femoral component is typically placed on a patient's distal femur after appropriate resection, and the tibial component is typically placed on a patient's tibial plateau after appropriate preparation. Various adjustments may be made to the cuts on either the tibial or femoral surface and different component sizes are considered. During this process, the knee is flexed and extended in order to determine the appropriate size, fit, and adjustment for the components. The surgeon may interchange various trial components in order to determine the appropriate size and fit for the implant.

More specifically, trial prostheses are used for trying the fit of the actual prosthesis or implant components to respective portions of the joint. After shaping the femur and tibia, the surgeon may temporarily fit trial components instead of the actual prosthetic components to the femur and/or tibia. This enables the surgeon to test the fit and performance of the components both statically and dynamically throughout a desired range of motion. Use of trial prosthetics instead of the actual implant allows the surgeon to perform this testing and achieve a more perfect fit and a more accurate performance of the actual component without introducing the actual prosthetic components into the surgical field. Although surgeons use various imaging techniques and palpation to study a particular patient's anatomy prior to surgery, they nevertheless gain considerable information required to fit the prosthetic components after the knee has been surgically exposed and the surgery has begun.

Accurately positioning and fitting the prosthetic components is important for a number of reasons. First, each patient has a different bone structure and geometry. Also, motion of the tibia relative to the femur about every axis varies from one patient to the next. Further, some knee replacement patients may have functionality problems with medial/lateral, anterior/posterior, or varus/valgus ligaments, and an implant that constrains the movement of the knee joint may be needed to enhance stability. In these instances, the surgeon may need to use a femoral implant with a constrained box geometry to ensure stability of the knee once the ligaments have been released.

Many systems for such a cruciate ligament sacrificing procedure use a constraining box geometry cutting block/guide and a separate femoral trial in order to prepare the bone to receive a permanent implant and then test the fit. In this process, the surgeon makes the initial cut(s) using a cutting block that is placed on the femur. Such cutting blocks are typically square (i.e., they are not shaped like the actual implant) and may be secured in place on the resected femur. Anterior and posterior chamfer resections are then made to shape the bone to receive the inner portion (i.e., the "box portion") of the femoral component. Femoral box resection cuts then need to be made. Typically, a separate femoral box cutting guide is secured on the surface of the femoral bone, and a reciprocating saw and/or box chisel is used to remove medial, lateral, and proximal (and anterior in some instances) portions of bone in the notch. Then, for trial reduction, the cutting guide is removed and a femoral trial component with box geometry built-in to the component is secured on the prepared femur. A tibial tray is placed on the prepared tibia and if necessary, a trial patellar component is also selected. Once the components are in place, the surgeon checks the range of motion and stability of the knee.

However, using a separate constraining box cutting guide and then a separate trialing component can add to surgery time, forces the surgeon to do more guessing, and is generally less efficient than if the cutting and trialing process could be accomplished with a single component. Some implant designers have attempted to solve this problem by providing variously sized adapters that can be screwed into the femoral trial component, some adapters allowing for a cruciate retaining procedure and others allowing for a cruciate sacrificing procedure. See, e.g., U.S. Pat. No. 5,776,201, issued to Johnson & Johnson Professional, Inc. on Jul. 7, 1998. Others have provided a spanning member that can be locked in place with a sliding retention member. See, e.g., U.S. Pat. No. 6,827,739, issued to Zimmer Technology, Inc. on Dec. 7, 2004. However, in order to use these systems, the femoral trial needs to be removed from the operating envelope in order to assemble the adapter or spanning member to the component, and then a reinsertion is required. In short, both of these systems cooperate with the inner or proximal portion of the femoral trial.

Embodiments of the present invention help solve these problems by providing a femoral trial component that can be used as a guide for the box cut, and that can then be completed with a cam module—without removal from the patient's bone—so that the same component can be used for the trialing process. One way this may be accomplished is by providing a cam module that can cooperate with an outer distal aspect, portion, or side of the femoral trial component so that the component does not need to be removed for trialing preparation steps.

SUMMARY

The systems and methods described help a surgeon prepare a patient's bone to receive a permanent implant by providing a system that can be used to guide preparatory box cuts, and that can then be completed with a cam module, without removing the system from the patient's bone, so that the same component can be used for the trialing process.

One aspect of the present invention provides a femoral trial component cam module, comprising:
(a) a body portion having a medial wall and a lateral wall;
(b) one or more shoulders extending from an upper portion of the medial or lateral walls, the one or more shoulders adapted to cooperate with a femoral trial component; and
(c) a cam member extending between a posterior portion of the medial wall and the lateral wall.

In one embodiment, the cam module further comprises an anterior wall, wherein the one or more shoulders extends from an upper portion of the medial, lateral, or anterior walls.

In another embodiment, the cam module further comprises a base portion between the medial and lateral walls.

In a further embodiment, the one or more shoulders of the cam module further comprise pivot pegs.

A further embodiment provides an opening between the medial and lateral walls.

Another embodiment further comprises a trial tibial component having a post that is adapted to be received by the opening of the cam module.

In a further embodiment, the cam module further comprises a retention system that cooperates with a distal aspect of a femoral trial component.

In some embodiments, the retention system comprises at least one resilient arm and at least one retention member associated with the resilient arm, such that in use, the resilient arm is depressed upon insertion of the cam module into a femoral trial component, allowing the retention member to cooperate with a corresponding structure on the femoral trial component.

In other embodiments, the retention system comprises a spring-loaded system.

A further embodiment includes a cam module with a rotational stop. In some embodiments, the rotational stop extends from upper portions of the medial and lateral walls and forms a ledge that abuts a femoral component in use. Inn further embodiments, the rotational stop abuts a track on the femoral component.

Another embodiment further provides a femoral component having one or more resection slots formed therein. The femoral component may also comprise one or more receiving portions that receive the one or more shoulders of the cam module. The femoral component may further comprise one or more securing holes formed therein.

Other embodiments of the invention provides the cam module as a component of a kit comprising one or more femoral trial components, one or more tibial trial components, one or more actual femoral implants, one or more actual tibial implants, or any combination thereof.

Another embodiment provides a cam module that is adapted to cooperate with a distal aspect of a femoral trial component without removal of the femoral trial component from a patient's bone.

Other aspects of the present invention provide a method of preparing a femur to receive a final implant, comprising:
(a) providing a femoral trial component with an outer distal side and an inner proximal side, the femoral trial component having
 (i) resection slots formed in the trial component;
 (ii) femoral condylar components separated by an opening, and
 (iii) one or more receiving portions on the outer distal side for receiving shoulders of a cam module;
(b) placing the femoral trial on a resected femur and preparing additional cuts, including using the opening for preparing box cuts;
(c) providing a cam module having
 (i) a body portion having a medial wall and a lateral wall;
 (ii) one or more shoulders extending from an upper portion of the medial or lateral wall, the one or more shoulders adapted to cooperate with the one or more receiving portions of femoral trial component; and
 (iii) a cam member extending between a posterior portion of the medial wall and the lateral wall;
(d) placing the one or more shoulders of the cam module into the one or more receiving portions of the femoral trial so that the cam module fits in the opening of the femoral trial.

Some embodiments of these methods include the cam module being adapted to cooperate with the femoral trial component without removal of the femoral trial component from a patient's bone.

Other embodiments further comprise:
(e) providing a tibial component having a post;
(f) placing the tibial component on a prepared tibial plateau;
(g) inserting the post of the tibial component between the medial and lateral walls of the cam module; and
(h) trialing the femoral component and tibial component by extending and flexing a patient's knee.

Other aspects of the present invention relate to a system for preparing a femur to receive a final implant, comprising:
(a) a femoral trial component comprising
 (i) femoral condylar components separated by an opening, and
 (ii) one or more receiving portions on a distal aspect of the femoral trial component for receiving shoulders of a cam module;
(b) a cam module comprising
 (i) a body portion having a medial wall and a lateral wall;
 (ii) one or more shoulders extending from an upper portion of the medial or lateral wall, the one or more shoulders adapted to cooperate with the femoral trial component; and
 (iii) a cam member extending between a posterior portion of the medial wall and the lateral wall;
wherein the one or more shoulders of the cam module are adapted to be secured by the one or more receiving portions of the femoral trial so that the cam module fits in the opening of the femoral trial.

Embodiments of such systems may provide a plurality of femoral trial components in various sizes, a plurality of cam modules in various sizes, or a combination thereof.

Other embodiments further comprise a tibial trial component having a post, wherein the post is adapted to be received by an opening located in the cam module anterior to the cam member.

Another embodiment of the system provides a plurality of femoral trial components in various sizes, a plurality of cam modules in various sizes, a plurality of tibial trial components in various sizes, or a combination thereof.

A further embodiment provides a cam module that is adapted to cooperate with the femoral trial component without removal of the femoral trial component from a patient's bone.

Another embodiment provides a femoral trial component that has resection slots formed therein.

One specific aspect of the invention provides a femoral trial component cam module, comprising:
(a) a body portion having a medial wall, a lateral wall, an anterior wall, and an opening;

(b) one or more shoulders extending from an upper portion of the medial or lateral walls, the one or more shoulders adapted to cooperate with a femoral trial component and comprising pivot pegs;
(c) a cam member extending between a posterior portion of the medial wall and the lateral wall;
(d) a retention system for securing the cam module with an outer distal side of a femoral component; and
(e) a rotational stop that extends from upper portions of the medial and lateral walls that forms a ledge to abut a track of a femoral component;
   wherein the cam module is adapted to cooperate with a femoral trial component without removal of the femoral trial component from a patient's bone.

"Embodiment" as used herein can be considered to mean an "aspect" or "object of the invention" and vice versa.

DETAILED DESCRIPTION OF THE INVENTION

Embodiments of the present invention provide systems and methods that allow a surgeon to prepare a patient's femur to receive a femoral component more efficiently. One embodiment provides a femoral trial component that can be used to make constraining box geometry cuts, and that can then be completed with a cam module, without removing the trial component, for the trialing step. This system prevents the need to first use a cutting guide to prepare the femur and then remove the cutting guide and replace it with the trial component for the trialing process. It reduces operating room time, and also reduces the need for multiple invasions of the operating envelope (replacing and removing components), decreasing the potential for infection and other complications.

Figure 1:
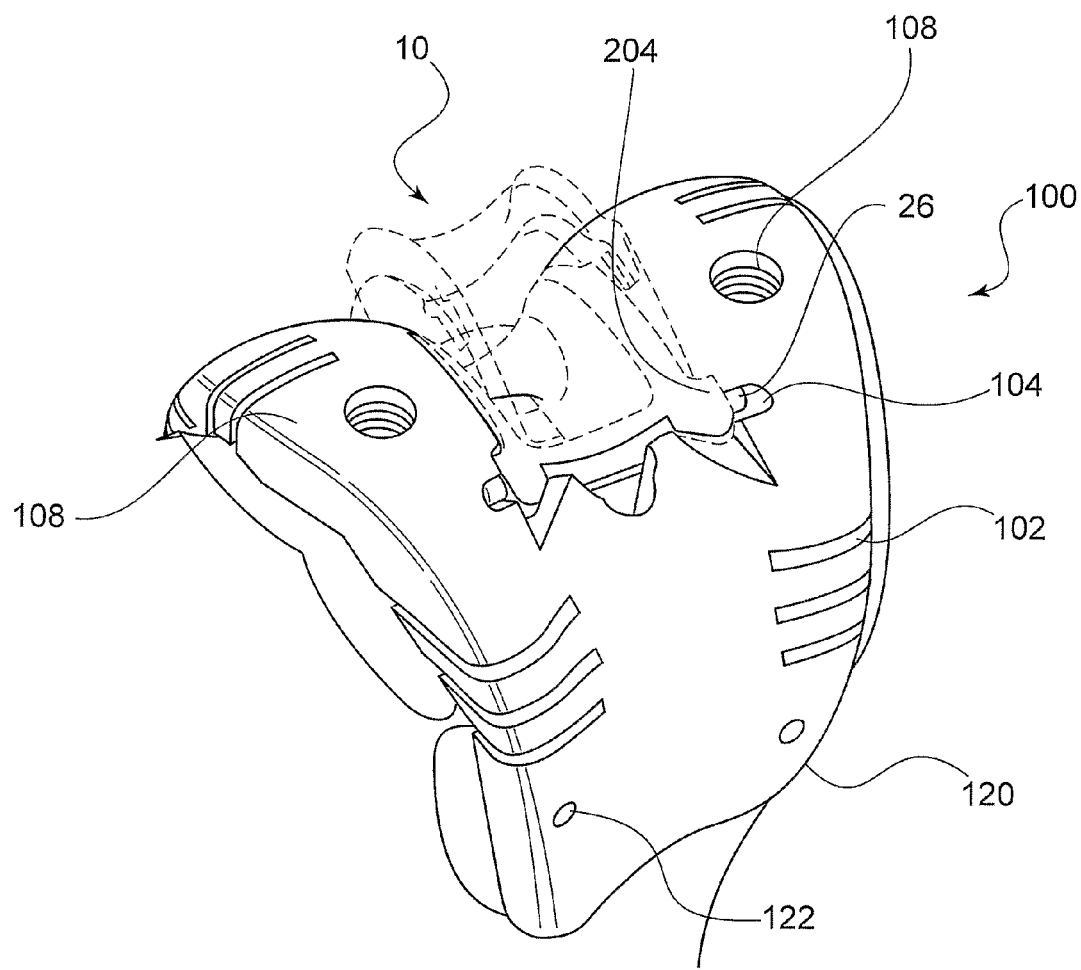
FIG. 1 shows a front perspective view of a cam module being positioned in a femoral trial component.
Figure 4:
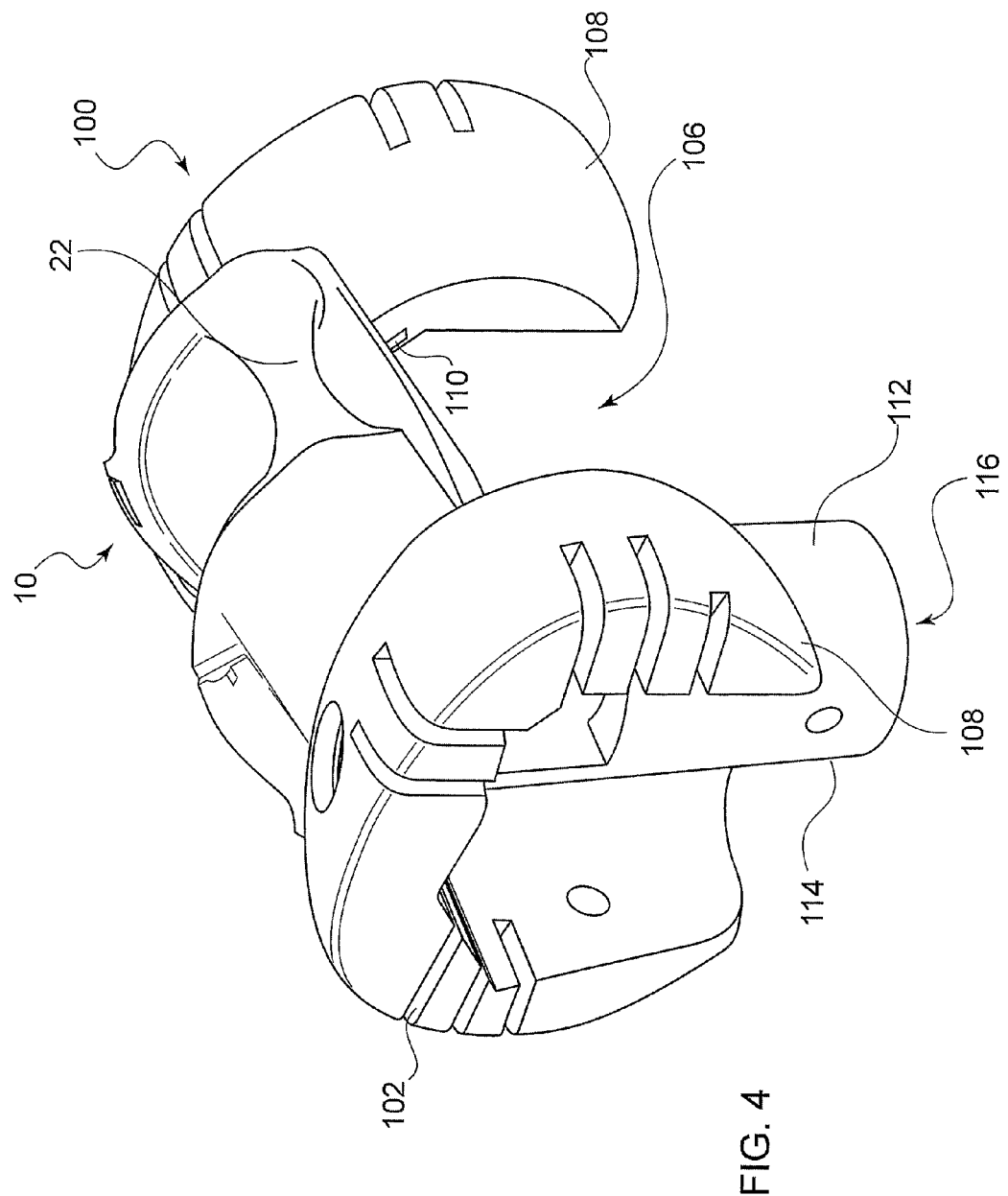
FIG. 4 shows a back perspective view of a cam module being positioned in a femoral trial component.

As shown in FIG. 1, there is provided a femoral trial component 100 and a cam module 10 component. These components may be made out of any material that is appropriate for trialing purposes, for example metals such as zirconium, cobalt-chrome, stainless steel, titanium, or even polyethylene or other types of strong plastics or composites, such as graphites and polymers. The femoral trial component 100 has a J-shaped cross section, with the upper part of the "J" forming the anterior portion 120 and the hooks of the "J" forming the condyles 108 of the component 100. This is perhaps shown more clearly in the perspective view of FIG. 4. As shown in FIG. 4, trial component 100 may also have a stem portion 112, which can be a protrusion 114 with an opening 116 to receive a stem (not shown) that is received in a patient's intramedullary canal in order to secure component 100 in place. This allows trial component 100 to be trialed with various types of stems, such as offset stems, angled stems, and stems of various lengths and diameters.

Trial component 100 is shown having various resection slots 102. Although multiple slots are shown in certain orientations, it should be understood that any orientation of one or more slots is considered within the scope of this invention. During surgery, the surgeon may make various resections of the femur as needed. The surgeon may use slots 102 on trial component 100 to guide those resection cuts. Moreover, when module 10 is not in place, there is an opening 106 provided between condylar components 108. Opening 106 in trial 100 provides an access area through which instruments may pass in order to prepare box geometry cuts in the femur. The tracks 110 on trial 100 can be used to guide box cutting guides, chisels, and/or reamers. Preparation is needed in order for the box portion 152 of implant 150 to fit the bone appropriately. As example of a final implant 150 in shown in FIG. 10 for reference. As shown and discussed in more detail below, the box portion 152 of the implant cooperates 150 with post 162 of the trial component 160 in order to stabilize the knee.

Referring back to FIG. 1, in addition to resection slots 102, trial component 100 may also have one or more securing holes 122. Securing holes 122 are intended to receive fasteners or pins that can hold trial 100 in place on the patient's bone during surgery.

The ability to use a trial component shaped like the actual implant, but through which cuts may be made, is useful because it gives the surgeon visual cues with respect to an anterior/posterior, medial/lateral, and internal/external rotation of the femoral component. Then, once the cuts have been prepared but without removal of the trial 100 from the patient's bone, a cam module 10 can be inserted into opening 106 to complete the cruciate constraining geometry of the trial 100 for trialing purposes. This reduces operating time and reduces the need for multiple placement and removal steps for different types of cutting guides and trials, which can cause some of the above-described complications.

Figure 2:
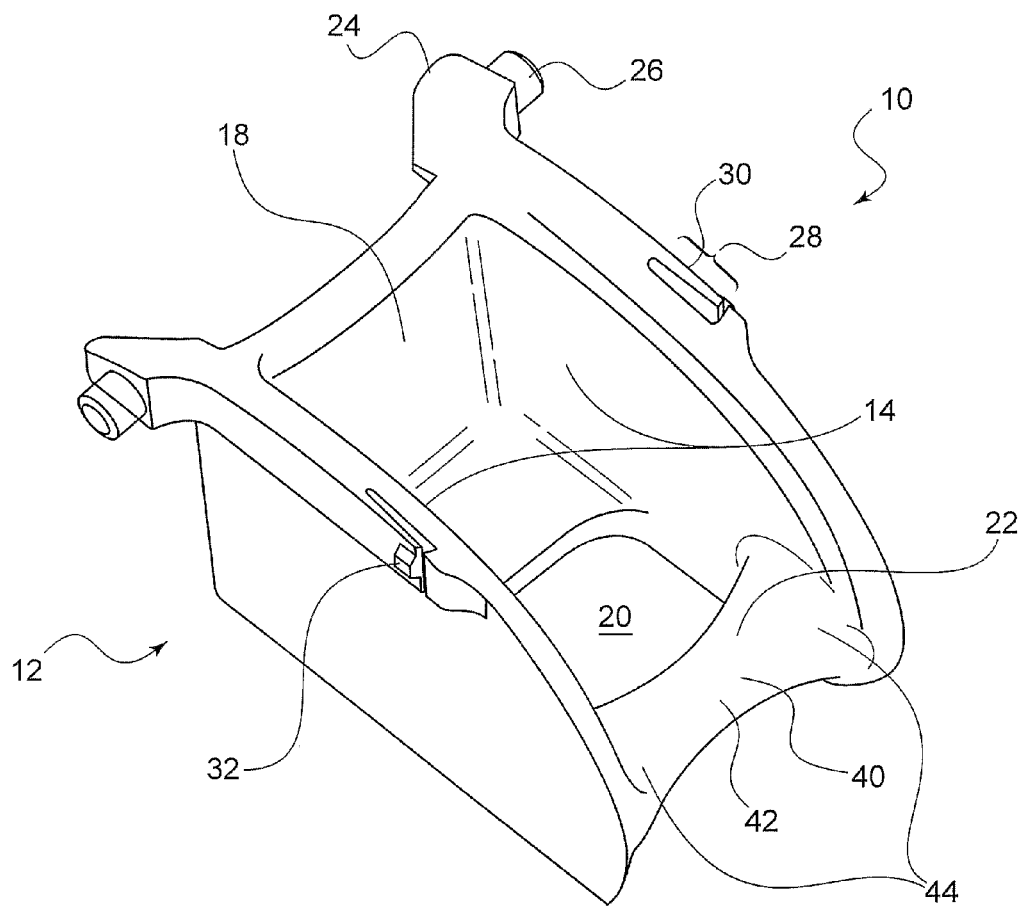
FIG. 2 shows a top perspective view of one embodiment of a cam module according to various aspects of the invention.

As discussed, cam module 10 cooperates with and completes trial 100. An example of one embodiment of a cam module 10 is shown in FIG. 2. Module 10 is shown having a body portion 12 that is defined by medial and lateral walls 14, a base portion 16, an anterior wall 18, an opening 20, and a cam member 22. (Modules may be provides with fewer walls than those described.) It is possible to provide various embodiments of modules that have different spacing and heights between walls 14 and 18, base portion 16, and cam member 22 to correspond to differently-sized implants. It is also possible, however, to provide different sizes of femoral trials 100 that all cooperate with the same size cam module 10—this can prevent the need for additional, multiple cam module components during the surgery. As described in more detail below, the body portion of 12 of cam module 10 essentially defines one or more walls to form a box that stabilizes or constrains knee movements in a cruciate sacrificing knee replacement procedure surgery.

Figure 6:
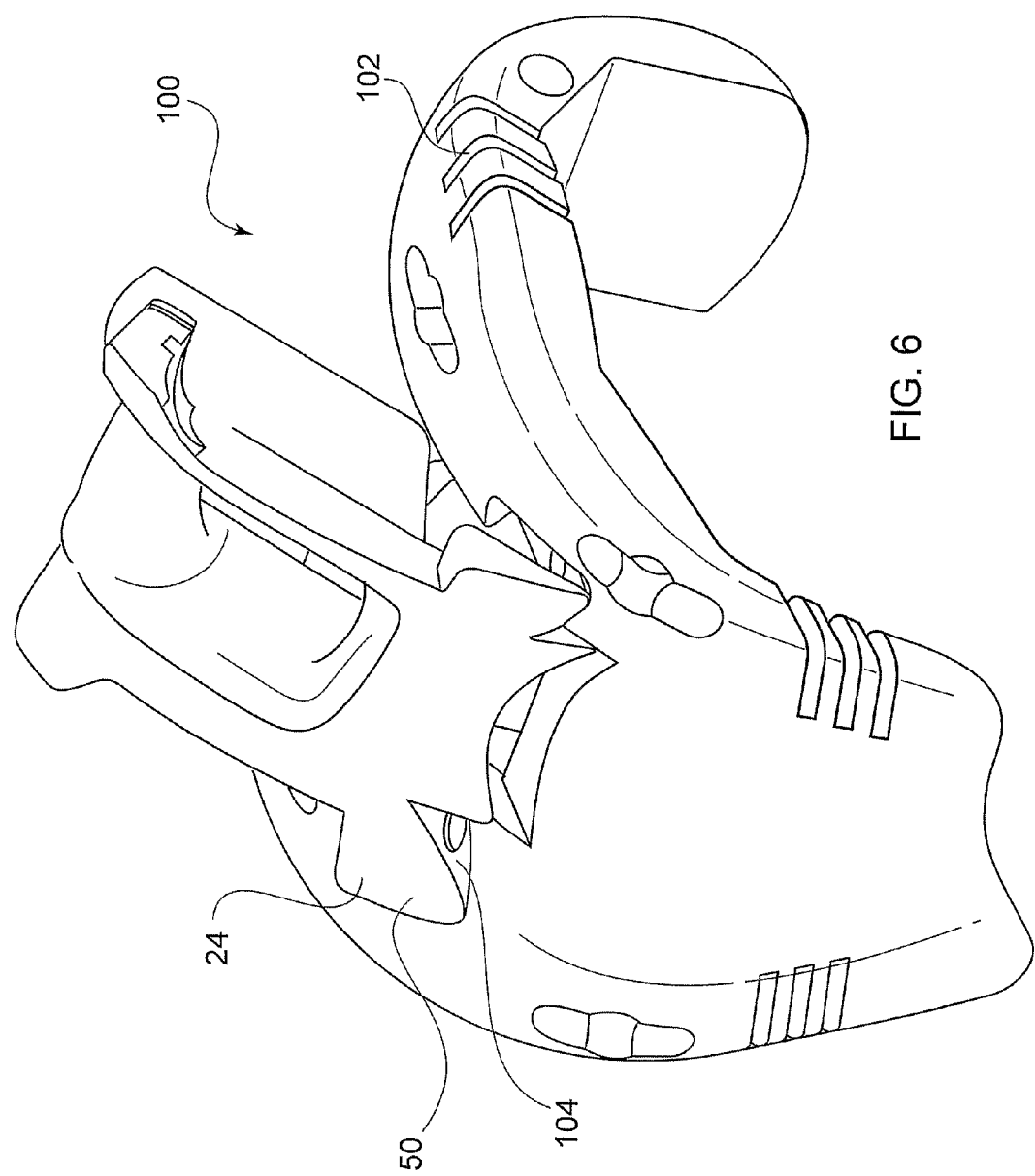
FIG. 6 shows an alternate embodiment of a cam module being positioned in a femoral trial component.

Extending anteriorly from body portion 12, and in some embodiments, from medial and lateral walls 14, are shoulders 24. Shoulders 24 may have optional pivot pegs 26 that help place and secure shoulders 24 in receiving portion 104 of trial component 100, as shown in FIG. 1. Although pivot pegs 26 can be useful, it is possible to provide a cam module without such pegs, as shown in FIG. 6. Instead of pivot pegs, the shoulders 24 of the cam module shown in FIG. 6 may be shaped like wings 50 that fit into and cooperate with receiving portion 104 of trial 100. It should be understood that other securing mechanisms may be used to achieve cooperation between the trial 100 and the cam module 100, such as a dovetail slot, a J-hook lock, ball and detent mechanism, a magnetic lock, a snap or push lock, or any other appropriate locking or securing mechanism. If other securing mechanisms are used, it should be understood that the shoulders 24 of cam module 10 and receiving portions 104 of trial component 100 should be shaped appropriately so that they fit with and correspond to one another. The general intent is that cam module 10 can be easily and securely held in the trial 100, and also relatively easily removed if additional bone preparation is needed.

Figure 3:
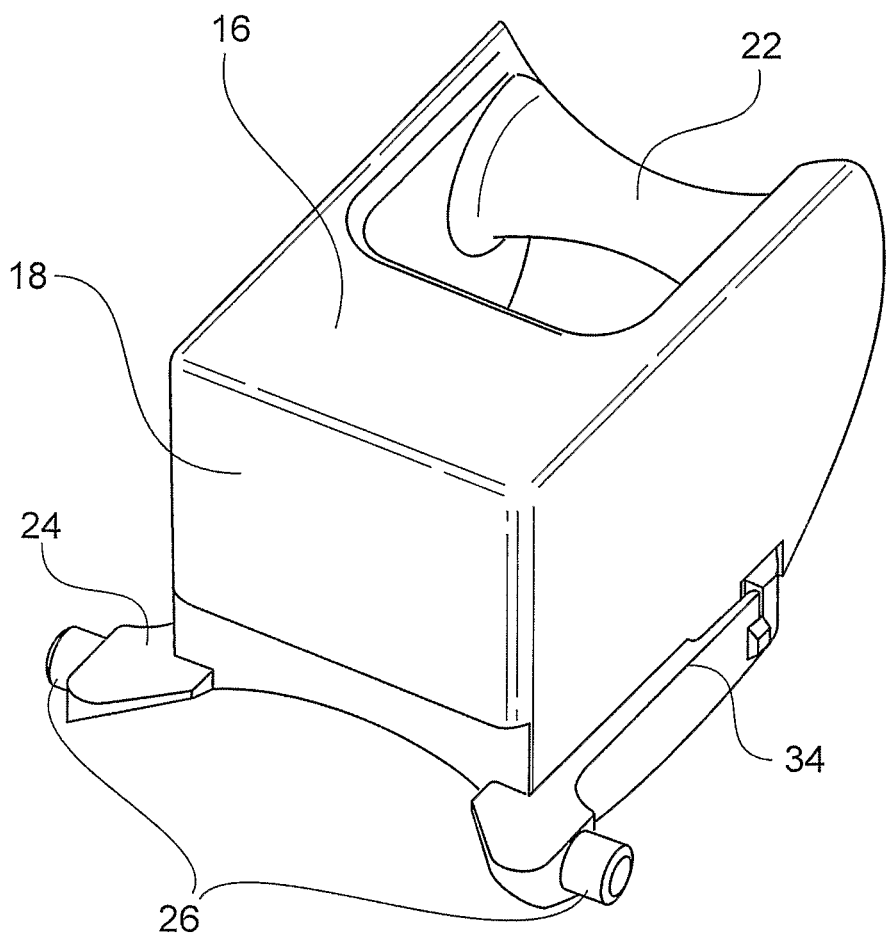
FIG. 3 shows a bottom perspective view of the cam module of FIG. 2.

When shoulders 24 and optional pivot pegs 26 register with receiving portion 104 of trial 100, they limit movement of the cam module 10 in all directions—except that they allow anterior/superior rotation of module 10 about the pivot pegs 26. The rotation of cam module 10 is stopped by rotation stop 34, on the undersurface of cam module, as shown in FIG. 3. In use, rotation stop 34 may abut track 110 of trial 100, as shown in FIG. 4, to stop further rotational movement of module 10.

The cam module 10 is then retained and secured in position in the trial component 100 by retention system 28. Retention system 28 and the shoulder 24/receiving portion 104 interface are both designed so that the cam module is retained at the outer distal aspect 118 (also referred to as outer distal side or distal portion) of the femoral trial 100 (e.g., the outer surface of the trial at the distal end) as opposed to the inner proximal surface (e.g., the inside portion that interfaces with bone). Securing the cam module at the outer distal aspect 118 allows cam module 10 to be assembled with trial 100 when trial is in position on a patient's bone. (This is in contrast to some currently-available systems, which provide adapters that cooperate only with the proximal aspect of a femoral trial component, e.g., by threaded screws that secure an adapter to a trial, as shown in U.S. Pat. No. 5,776,201. One of the problems with this prior art configuration is that the proximal aspect of the trial is actually concealed by bone when the trial is in place on the femur so that in order to use the adapter during surgery, the trial needs to be removed from the patient's bone, the adapter inserted, and the trial replaced on bone, which causes some of the problems described above.) One example of a retention system at the distal aspect 118 of the module 10 and trial 100 is shown in FIG. 2. An example of an alternate retention system 28 is shown in FIGS. 7-9.

Figure 5:
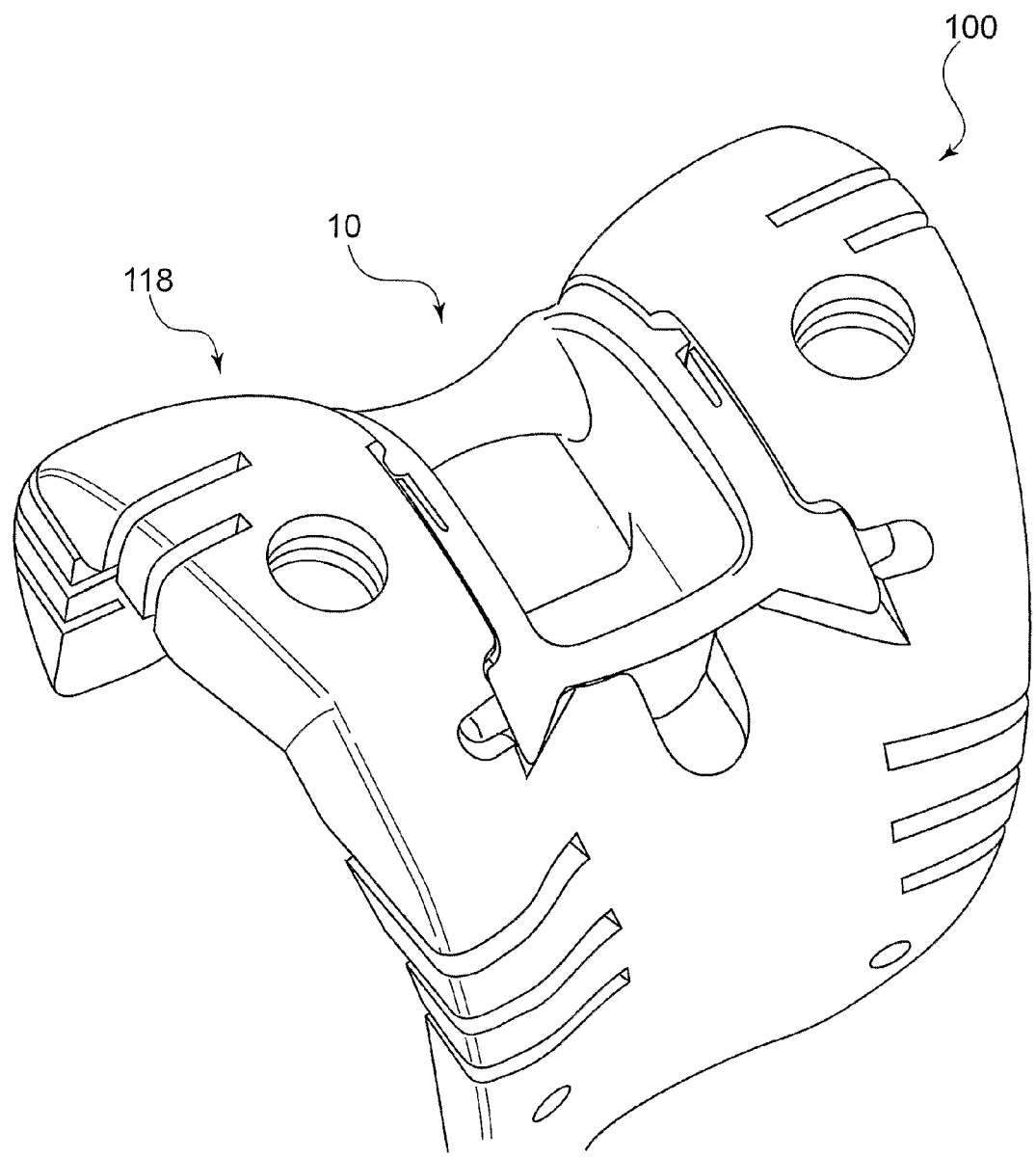
FIG. 5 shows a top perspective view of a cam module secured with respect to a femoral trial component.

Referring now to FIG. 2, one embodiment of retention system 28 may feature resilient arms 30 and a retention member 32. In use, resilient arms 30 are depressed inwardly (toward the medial and lateral walls 14). Once cam module 10 is fully inserted, the arms 30 relax back to their neutral position against the trial 100 in order to secure module 10 in place. Retention member 32 may also be provided, which can act as a tab for additional securement by pressing against the trial 100 to hold module 10 in place. An example of this system 28 in use is shown in FIG. 5.

Figure 7:
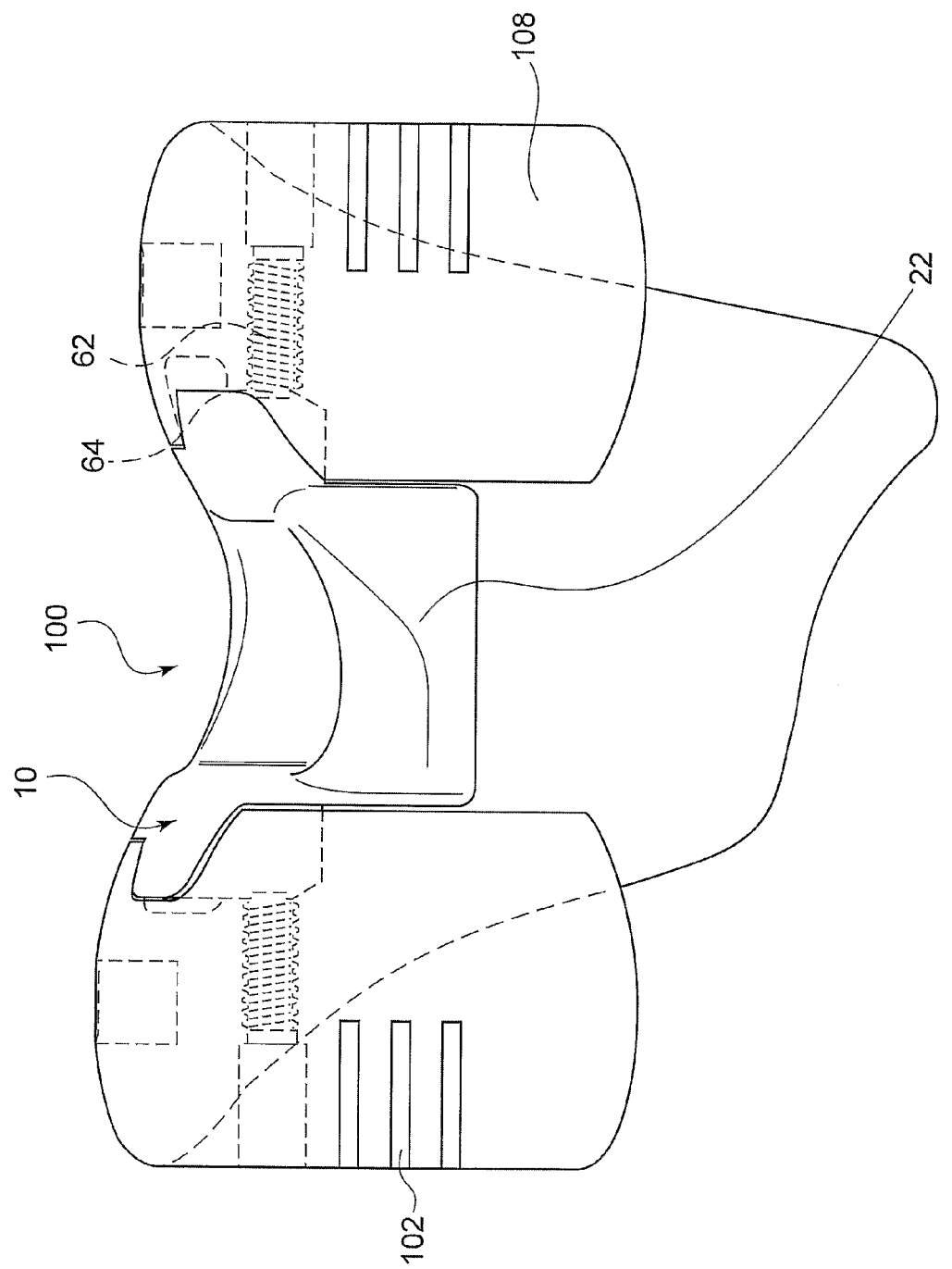
FIG. 7 shows a front cross-sectional view of a cam module being held in place with respect to a femoral component via a spring-loaded system.
Figure 9:
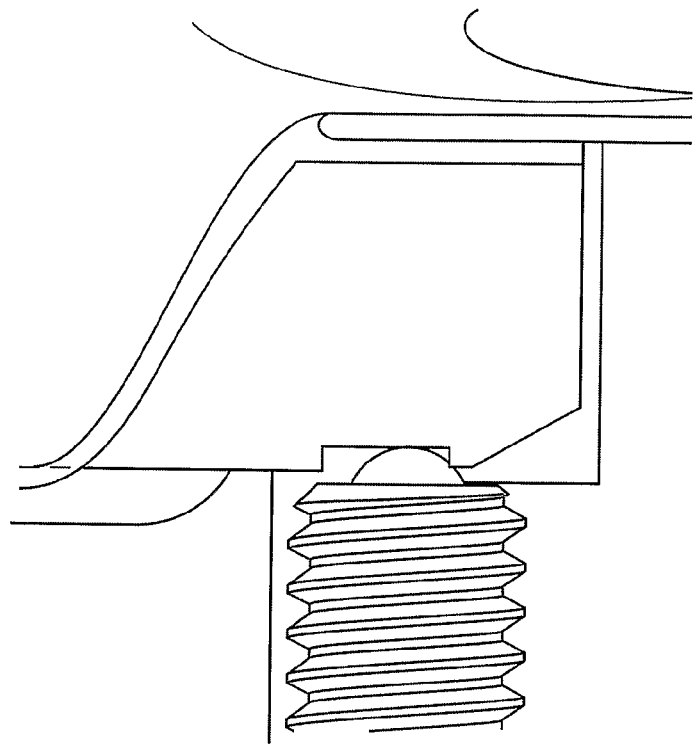
FIG. 9 shows a close-up view of the spring-loaded system of FIG. 7, after the cam module has been locked into place.
Figure 8:
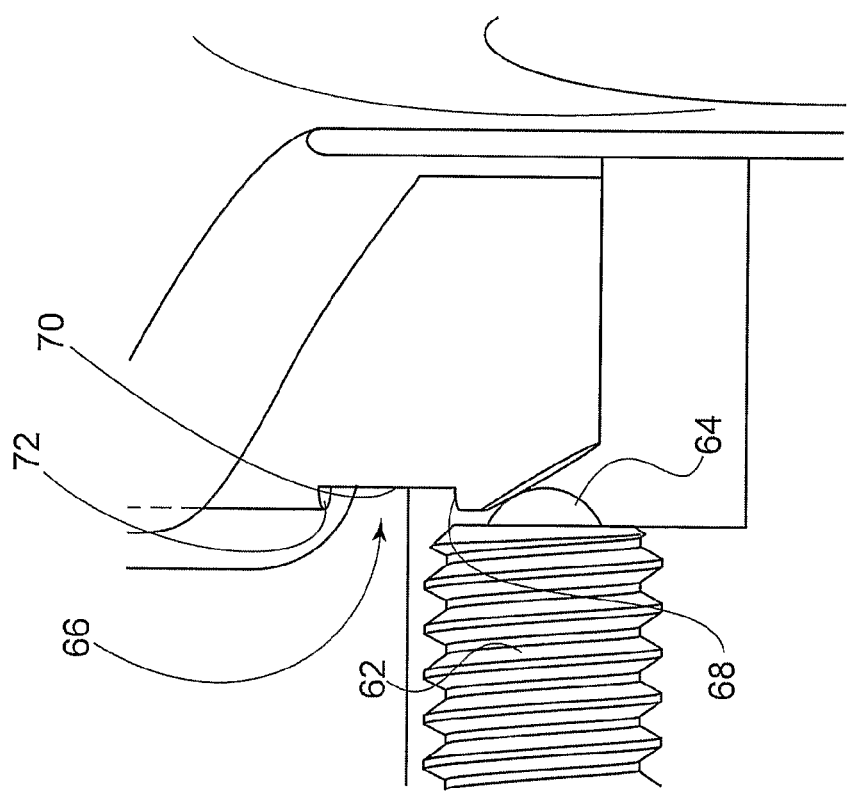
FIG. 8 shows a close-up view of the spring-loaded system of FIG. 7, before the cam module is secured into place.

An alternate retention system is shown in FIGS. 7-9. That system may feature a spring-loaded system 60 that includes one or more springs 62 embedded in the condyle portions 108 of the femoral trial as shown. At the end of spring is a protrusion 64. As shown in FIG. 8, cam module 10 may have a receiving portion 66 that includes a lower ledge 68, an indented portion 70, and an upper ledge 72. As cam module 10 is rotated into position, the lower ledge 68 pushes the spring 62 outward, and as the module is pressed into place, the protrusion 64 at the end of spring 62 slides over the lower ledge 68, and is allowed to rest in the indented portion 70 of the cam module receiving portion. Because the spring 62 is resilient, the module 10 can easily be removed and replaced if necessary. An example of this system in use in shown in FIG. 9.

Although two exemplary connection mechanisms have been described, it should be understood that any connection system that allows cam module 10 to be removably locked, secured, or received by femoral trial component 100 such that it is no longer able to rotate about its shoulders 24 should be considered within the scope of this invention. For example, the components could snap together, be magnetized to secure together, be secured by a ball and detent mechanism, have a J-hook lock, have a dovetail slot and track, or connect at this back portion by any other appropriate way.

Referring back to FIG. 2, cam module 22 also has a cam member 22 at its posterior end. Cam member 22 is essentially a thin bar 40 that extends between posterior ends of medial and lateral walls 14. As shown, cam member 22 may have a smaller circumference (or be more eccentric) at its middle part 42 than at its outer ends 44. This can help achieve knee kinematics similar to those that are achieved with the actual implant. The thicker portions at the ends can also help secure outer ends 44 to walls 14. Cam member 22 is provided to replicate the cam of the actual implant, shown in FIG. 10.

Figure 10:
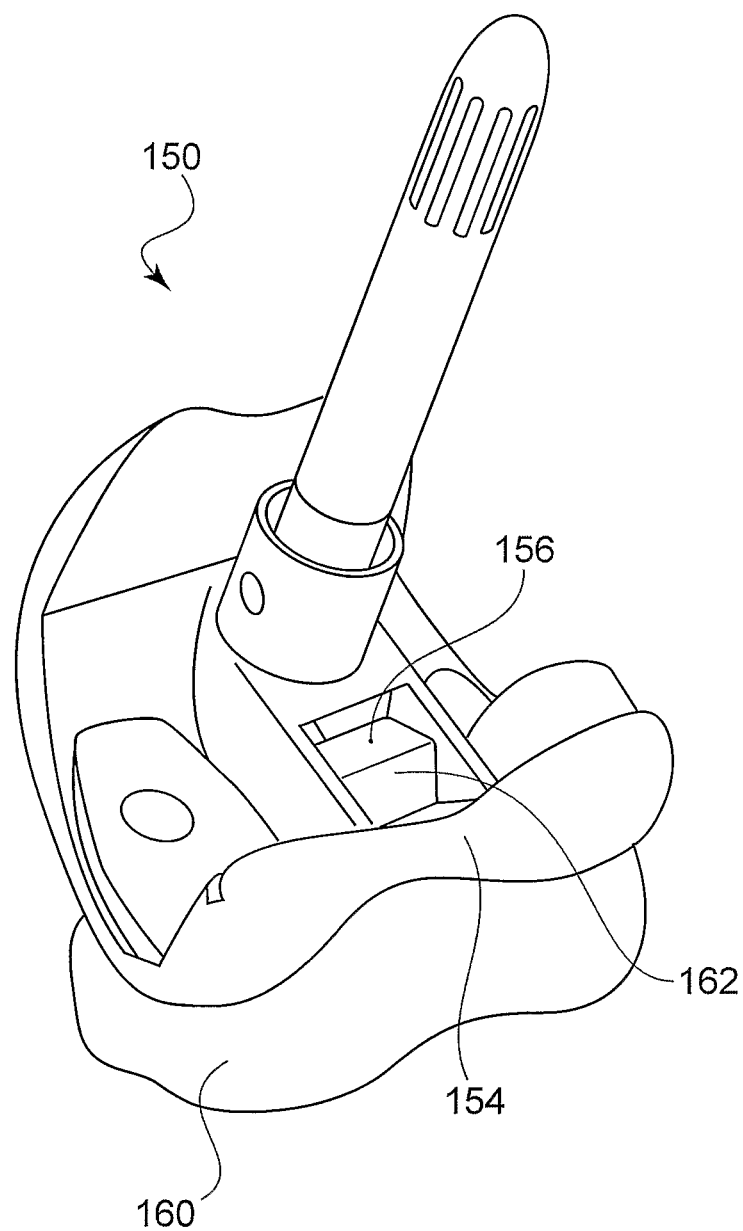
FIG. 10 shows an example of a permanent implant to be placed on the femur once it has been prepared and the proper component fit has been determined by trialing.
Figure 11:
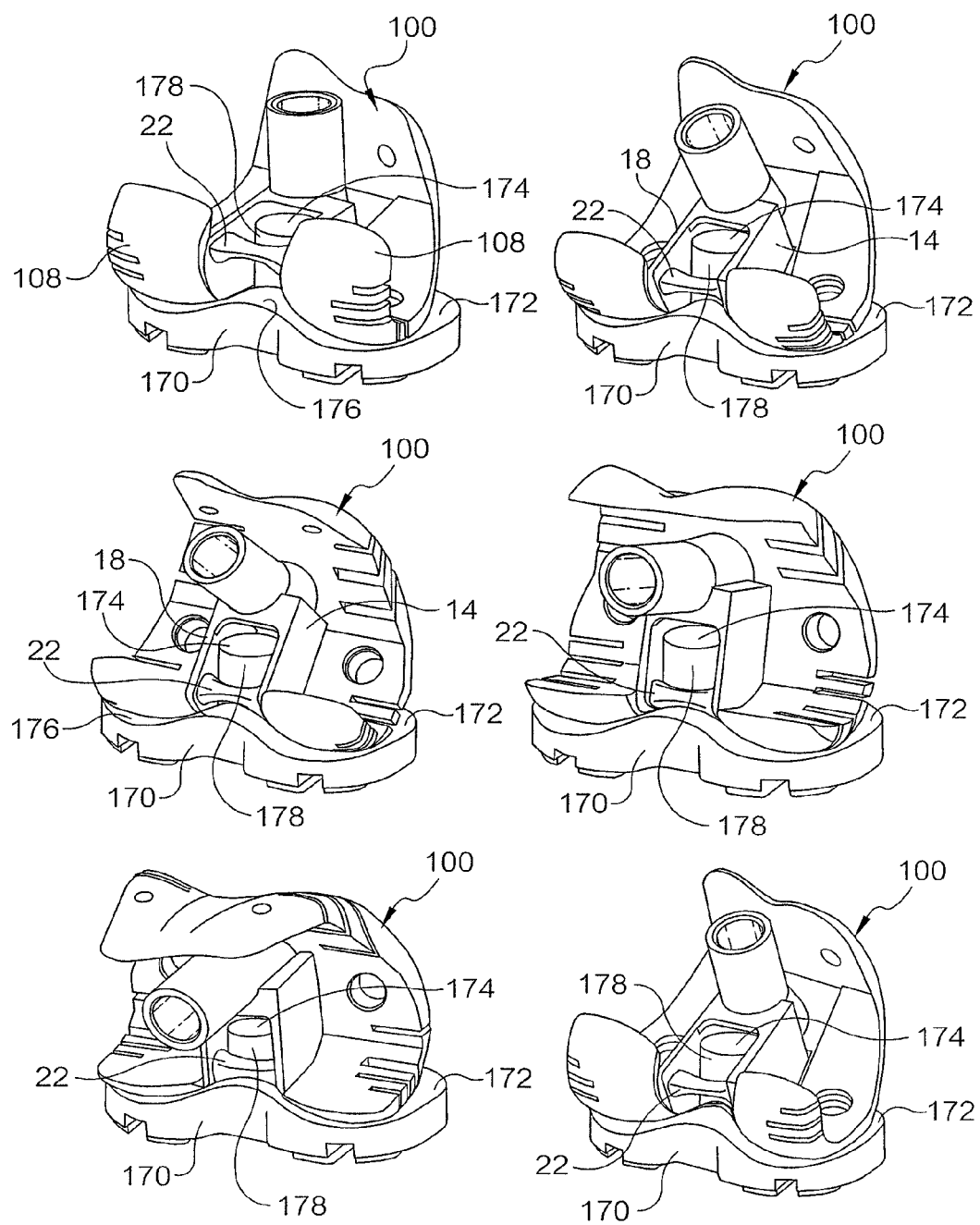
FIG. 11 illustrates the interaction between the cam module and the tibial trial post during trialing.

FIG. 10 shows implant 150 and how it cooperates with a tibial component (or bearing insert) 160 once the actual components are in place. For perspective, FIG. 11 illustrates the interaction between the cam module and the tibial trial post during trialing. As shown, the condyles 108 of femoral trial component 100 sit against a bearing surface 172 of trial tibial component or bearing insert 170 (both referred to as component 170 for the sake of convenience). Component 170 has a post 174 extending up from its superior surface 176, i.e., the surface that does not face a patient's bone in use. The cam member 22 of the femoral trial 100 rests against a posterior portion 178 of the post 174. During trialing, the femoral trial 100 is rotated back (causing the cam member 22 to cooperate with post 174) in order to determine the proper fit. Medial, lateral and anterior walls 14, 18 all help to constrain the post 174 in place.

Specifically, during trialing there is provided a femoral trial component with an outer distal side and an inner proximal side, the femoral trial component having (i) resection slots formed in the trial component; (ii) femoral condylar components separated by an opening, and (iii) one or more receiving portions on the outer distal side for receiving shoulders of a cam module. The surgeon places the femoral trial on a resected femur and prepares additional cuts, including using the opening for preparing box cuts. The surgeon these selects a cam module having (i) a body portion having a medial wall and a lateral wall; (ii) one or more shoulders extending from an upper portion of the medial or lateral wall, the one or more shoulders adapted to cooperate with the one or more receiving portions of femoral trial component; and (iii) a cam member extending between a posterior portion of the medial wall and the lateral wall. The surgeon places the one or more shoulders of the cam module into the one or more receiving portions of the femoral trial so that the cam module fits in the opening of the femoral trial at the outer distal side.

Some embodiments of these methods include the cam module being adapted to cooperate with the femoral trial component without removal of the femoral trial component from a patient's bone.

Other embodiments further comprise (e) providing a tibial component having a post; (f) placing the tibial component on a prepared tibial plateau; (g) inserting the post of the tibial component between the medial and lateral walls of the cam module; and (h) trialing the femoral component and tibial component by extending and flexing a patient's knee.

Figure 12:
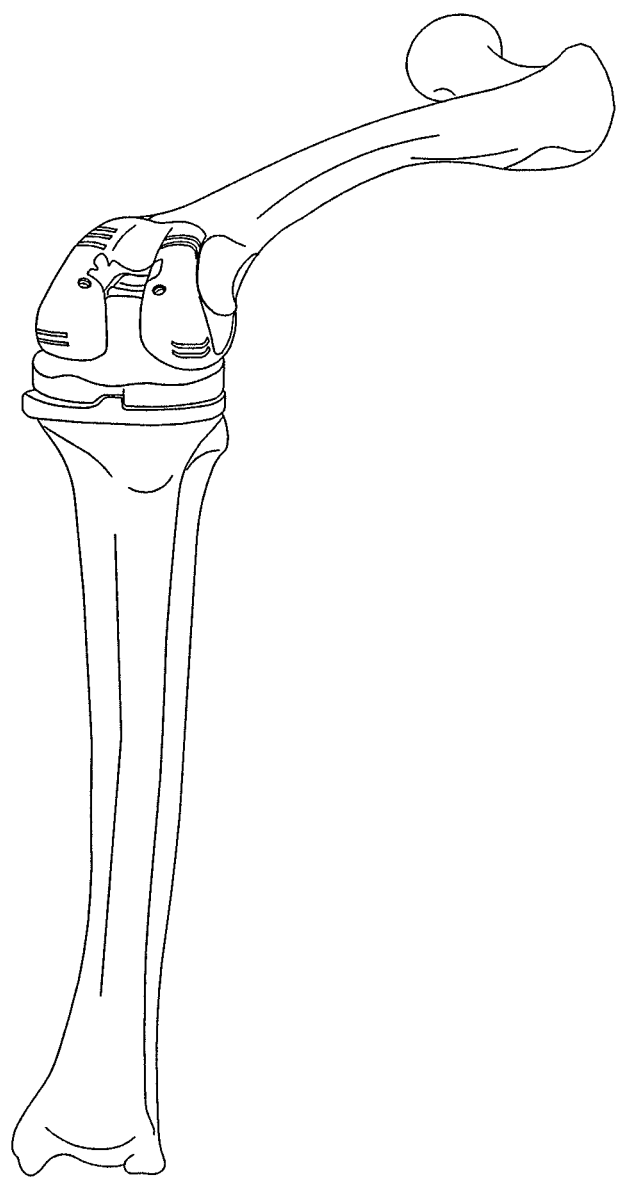
FIG. 12 shows a front perspective view of a femoral trial and tibial trial in place on a patient's bone.

FIG. 12 shows a front view of a completed trial system in place on a patient's knee and in use.

Once the trialing step has been accomplished, the surgeon determines the proper implants sizes to be used. Femoral components are usually metallic, having a highly polished outer condylar articulating surface. For example, they may be zirconium, titanium, stainless steel, cobalt-chrome or any other appropriate material that provides sufficient stability and biocompatibility. It should be noted that, although rare, ceramics may also be used. Tibial components may also be made of any of the above materials, and bearing inserts are often polyethylene (e.g., ultra high molecular weight polyethylene, which can reduce wear particles) or some other form of high density plastic.

Because the femoral component may cooperate with either a tibial component of a mobile bearing insert, both components are referred to in this description and FIG. 10 as component 160, to clarify that either may be used with various embodiments and considered within the scope of this invention. Component 160 is shown having a superiorly-directed post portion 162 that, in use, extends up through opening 156 of box portion 152 and cooperates with cam 154 of the implant 150 in use. An anterior portion of post 162 may abut medial and lateral walls of implant 150 (which correspond essentially to medial and lateral walls 14 of module 10). This system replaces the patient's natural posterior cruciate ligament if it is to be sacrificed during the procedure and helps maintain stability of the implant. The purpose for providing cam member 22 and opening 106 on the trial component 100 is to replicate the knee kinematics that occur between the cooperation of cam 154 and opening 156 with the post 162 of bearing 160. During trialing, the cam member 22 engages with a trial post when the knee is flexed to sublux (push) the tibia anteriorly, and the medial and lateral walls 14 engage trial post to prevent excessive lateral movement of the tibial and femoral components. In some instances, depending upon the design constraint, the anterior wall portion 18 may engage the trial post to prevent excessive hyperextension.

The trial component 100 (with cam module 10 in place) will then be trialed with a trial bearing component or a tibial trial component. (Although not shown, various trial bearings and/or tibial trial components may be used in connection with trial component 100 in order to determine the proper sizes for the ultimate components to be used.) The system is put through a range of motion in which different degrees of stability are assessed. The medial and lateral walls 14 constrain varus/valgus stability and, in part, rotational stability between the trial component 100 and the tibial trial or bearing. The cam member 22 is provided primarily to replicate constraint as a posterior cruciate ligament. The anterior wall 18 provides hyperextension stability.

The diversity of knee structure, geometry, and dynamics compels most suppliers of prosthetic components to offer a wide range of prosthetic options for knee replacement surgeries. These include, for instance, femoral and tibial components for primary surgeries as well as revision surgeries, porous coated and non-porous coated components, various sizes of stems for various tibial component plates, various femoral component interfaces for primary and revision cases, and prostheses which feature mobile bearings as well as those which do not. The present invention is intended for use with any of these options.

Changes and modifications, additions and deletions may be made to the structures and methods recited above and shown in the drawings without departing from the scope or spirit of the invention and the following claims.

What is claimed is:

1. A femoral trial component module for engagement with a femoral trial component, comprising:
   (a) a body portion having a medial wall and a lateral wall;
   (b) one or more shoulders extending anteriorly from an upper portion of the medial or lateral walls, the one or more shoulders adapted to cooperate with a femoral trial component having an outer distal side and an opposite inner proximal side configured to interface with femoral bone, the shoulders cooperating with a distal aspect of the femoral trial component and configured to rotate the module into position with respect to the femoral trial component from an outer distal location external to the femoral trial component and toward the femoral bone to assemble the module with the femoral trial component while the inner proximal side of the femoral trial component is positioned on the femoral bone; and
   a retention system including at least one resilient arm and at least one retention member associated with the resilient arm, wherein the resilient arm is depressed upon insertion of the module into the femoral trial component and allows the retention member to cooperate with a corresponding structure on the femoral trial component; and
   wherein the module and the femoral trial component are configured to be assembled to one another while the femoral trial component is attached to the femoral bone; and
   wherein the femoral trial component includes one or more openings extending inwardly from the outer distal side toward the opposite inner proximal side, the one or more openings sized for receipt of the one or more shoulders of the module therein.

2. A system for preparing a femur to receive a final implant, comprising:
   (a) a femoral trial component comprising
      (i) femoral condylar components separated by an opening, and
      (ii) an outer distal side, an opposite inner proximal side configured to interface with femoral bone, and two receiving portions on a distal aspect of the femoral trial component;
   (b) a module comprising
      (i) a body portion having a medial wall and a lateral wall; and
      (ii) two shoulders extending anteriorly from an upper portion of the medial or lateral wall, the shoulders each comprising a pivot element positioned in respective ones of the receiving portions of the femoral trial component and configured to rotate the module into position with respect to the femoral trial component from an outer distal location external to the femoral trial component and toward the femoral bone to assemble the module with the femoral trial component while the inner proximal side of the femoral trial component is positioned on the femoral bone, the body portion having an anterior end and an opposite posterior end, the shoulders located at the anterior end of the body portion and the posterior end of the body portion located between the femoral condylar components when the module is assembled with the femoral trial component wherein the shoulders of the module are adapted to be secured by the receiving portions of the femoral trial so that the module fits in the opening of the femoral trial; and wherein the module and the femoral trial component are configured to be assembled to one another while the femoral trial component is attached to the femoral bone; and wherein the receiving portions of the femoral trial component open onto an outer surface of the outer distal side and are sized for receipt of the shoulders of the module therein; and wherein the receiving portions comprise openings that open onto the outer surface of the femoral trial component opposite an inner bone interface surface of the femoral trial component; and wherein the shoulders of the module are positioned in the openings of the femoral trial component in a direction from the outer surface toward the inner bone interface surface; and wherein the module further comprises a retention system that cooperates with a distal aspect of the femoral trial component, and wherein the retention system comprises a spring-loaded system.

3. A system for preparing a femur to receive a final implant, comprising:
(a) a femoral trial component comprising
  (i) femoral condylar components separated by an opening, and
  (ii) an outer distal side, an opposite inner proximal side configured to interface with femoral bone, and two receiving portions on a distal aspect of the femoral trial component;
(b) a module comprising
  (i) a body portion having a medial wall and a lateral wall; and
  (ii) two shoulders extending anteriorly from an upper portion of the medial or lateral wall, the shoulders each comprising a pivot element positioned in respective ones of the receiving portions of the femoral trial component and configured to rotate the module into position with respect to the femoral trial component from an outer distal location external to the femoral trial component and toward the femoral bone to assemble the module with the femoral trial component while the inner proximal side of the femoral trial component is positioned on the femoral bone, the body portion having an anterior end and an opposite posterior end, the shoulders located at the anterior end of the body portion and the posterior end of the body portion located between the femoral condylar components when the module is assembled with the femoral trial component wherein the shoulders of the module are adapted to be secured by the receiving portions of the femoral trial so that the module fits in the opening of the femoral trial; and wherein the module and the femoral trial component are configured to be assembled to one another while the femoral trial component is attached to the femoral bone; and wherein the receiving portions of the femoral trial component open onto an outer surface of the outer distal side and are sized for receipt of the shoulders of the module therein; and wherein the receiving portions comprise openings that open onto the outer surface of the femoral trial component opposite an inner bone interface surface of the femoral trial component; and wherein the shoulders of the module are positioned in the openings of the femoral trial component in a direction from the outer surface toward the inner bone interface surface; and further comprising a retention system including at least one flexibly resilient arm that is flexibly depressed upon insertion of the module into the femoral trial component and cooperating with a corresponding structure on the femoral trial component to retain the module in engagement with the femoral trail component.

4. The system of claim 3, wherein the module further comprises an anterior wall, and wherein the shoulders extend from an upper portion of the medial, lateral, or anterior walls.

5. The system of claim 3, wherein the module further comprises a base portion between the medial and lateral walls.

6. The system of claim 3, wherein the pivot element comprises a pivot peg.

7. The system of claim 3, wherein the module further comprises an opening between the medial and lateral walls.

8. The system of claim 3, wherein the module further comprises a rotational stop.

9. The system of claim 8, wherein the rotational stop extends from upper portions of the medial and lateral walls and forms a ledge that abuts the femoral component in use.

10. The system of claim 8, wherein the rotational stop abuts a track on the femoral trial component.

11. The system of claim 3, wherein the femoral trial component further comprises one or more securing holes formed therein.

12. The system of claim 3, wherein the module is provided as a component of a kit comprising one or more femoral trial components, one or more tibial trial components, one or more actual femoral implants, one or more actual tibial implants, or any combination thereof.

13. The system of claim 3, wherein there is provided a plurality of the femoral trial components in various sizes, a plurality of modules in various sizes, or a combination thereof.

14. The system of claim 3, wherein the femoral trial component includes a plurality of elongate resection slots formed therein.

15. The system of claim 3, wherein the module further comprises (iii) a cam member extending between a posterior portion of the medial wall and the lateral wall; and
  wherein the cam member is positioned adjacent the posterior end of the body portion opposite the anterior end.

16. The system of claim 3, wherein the module and the femoral trial component are configured to be disassembled from one another while the femoral trial component is attached to the femoral bone.

17. A system for preparing a femur to receive a final implant, comprising:
(a) a femoral trial component comprising (i) femoral condylar components separated by an opening, and (ii) an outer distal side, an opposite inner proximal side configured to interface with femoral bone, and two receiving portions on a distal aspect of the femoral trial component;

(b) a module comprising (i) a body portion having a medial wall and a lateral wall; and (ii) two shoulders extending anteriorly from an upper portion of the medial or lateral wall, the shoulders each comprising a pivot element positioned in respective ones of the receiving portions of the femoral trial component and configured to rotate the module into position with respect to the femoral trial component from an outer distal location external to the femoral trial component and toward the femoral bone to assemble the module with the femoral trial component while the inner proximal side of the femoral trial component is positioned on the femoral bone, the body portion having an anterior end and an opposite posterior end, the shoulders located at the anterior end of the body portion and the posterior end of the body portion located between the femoral condylar components when the module is assembled with the femoral trial component wherein the shoulders of the module are adapted to be secured by the receiving portions of the femoral trial so that the module fits in the opening of the femoral trial; and wherein the shoulders of the module rotatably engage the femoral trial component at a location offset from the pair of femoral condylar components; and wherein the receiving portions comprise openings that open onto an outer surface of the femoral trial component opposite an inner bone interface surface of the femoral trial component; and wherein the shoulders of the module are positioned in the openings of the femoral trial component in a direction from the outer surface toward the inner bone interface surface; and further comprising a retention system including at least one flexibly resilient arm that is flexibly depressed upon insertion of the module into the femoral trial component and cooperating with a corresponding structure on the femoral trial component to retain the module in engagement with the femoral trail component.

18. The system of claim 17, wherein the module further comprises (iii) a cam member extending between a posterior portion of the medial wall and the lateral wall; and wherein the cam member is positioned adjacent the posterior end of the body portion opposite the anterior end.

* * * * *